US010918695B2

(12) United States Patent
Sharma et al.

(10) Patent No.: US 10,918,695 B2
(45) Date of Patent: Feb. 16, 2021

(54) USE OF JACK BEAN LECTIN FOR INCREASING THE ABUNDANCE OF HEMATOPOIETIC STEM CELLS AND PROGENITOR CELLS IN BONE MARROW AND/OR EPIDERMAL STEM CELLS IN SKIN IN VIVO

(71) Applicant: THE SECRETARY, DEPARTMENT OF ATOMIC ENERGY, Mumbai (IN)

(72) Inventors: Deepak Sharma, Mumbai (IN); Santosh Kumar Sandur, Mumbai (IN); Maikho Thoh, Mumbai (IN); Raghavendra Shridhar Patwardhan, Mumbai (IN); Dharmendra K. Maurya, Mumbai (IN); Rahul Checker, Mumbai (IN); Vikram P. Gota, Navi Mumbai (IN); Jayakumar Sundarraj, Mumbai (IN); Haldhar Dev Sarma, Mumbai (IN); Subrata Chattopadhyay, Mumbai (IN)

(73) Assignee: THE SECRETARY, DEPARTMENT OF ATOMIC ENERGY, Maharastra (IN)

( * ) Notice: Subject to any disclaimer, the term of this patent is extended or adjusted under 35 U.S.C. 154(b) by 31 days.

(21) Appl. No.: 16/239,280

(22) Filed: Jan. 3, 2019

(65) Prior Publication Data
US 2020/0215152 A1 Jul. 9, 2020

(51) Int. Cl.
*A61K 36/48* (2006.01)
*A61K 38/16* (2006.01)
*A61K 9/00* (2006.01)

(52) U.S. Cl.
CPC .......... *A61K 38/168* (2013.01); *A61K 9/0019* (2013.01); *A61K 36/48* (2013.01)

(58) Field of Classification Search
CPC ...... A61K 38/00; A61K 38/168; A61K 36/48; A61K 9/0019; C07K 14/415; C07K 14/42
See application file for complete search history.

(56) References Cited

FOREIGN PATENT DOCUMENTS

CA 2258503 12/1997

OTHER PUBLICATIONS

Fitzgerald et al. Comparison of the effects of concanavalin-A and epidermal growth factor on epithelial cell proliferation in the rat intestine. Aliment Pharmacol Ther 15: 1077-1084, 2001.*
Lin et al. Concanavalin A (NSC-143504): Its action on experimental tumor cells and possible use in cancer chemotherapy. Cancer Chemotherapy Reports 59(2): 319-326, 1975.*
Blasco E et al., "Proliferative response of human CD4' T lymphocytes stimulated by the lectin jacalin" European Journal of Immunology; Jul. 1995; vol. 25(7): pp. 2010-2018).
Boitano AE et al., "Aryl hydrocarbon receptor antagonists promote the expansionof human hematopoietic stem cell" Science Magazine, Sep. 10, 2010; vol. 329(5997):pp. 345-1348.
Bonomo et al., "A T Cell View of the Bone Marrow" May 2016; Frontiers in Immunology, 7: 184.
Brissot E et al., "Factors predicting allogeneic PBSCs yield after G-CSF treatment in healthy donors" Bone Marrow Transplant. Nov. 2009; vol. 44(9):pp. 613-615.
Broxmeyer HE et al., "Th1 cells regulate hematopoietic progenitor cell homeostasis by production of oncostatin M;" Immunity. 2002;16(6):815-25.
Greaves MF et al., "Activation of Human T and B Lymphocytes by Polyclonal Mitogens;" Nature Publishing Group, Apr. 19, 1974; vol. 248, pp. 698-701.
Kim M et al., "Lectin-induced apoptosis of tumour cells" Glycobiology. Oct. 1993 vol. 3 No. 5: pp. 447-453.
Liu K et al., "Chemical Modulation of Cell Fate in Stem Cell Therapeutics and Regenerative Medicine" Cell Chemical Biology; Aug. 18, 2016; 23(8):pp. 893-916.
Palacios R; "ConA triggers T lymphocytes by directly interacting with their receptors" Journal of Immunology. Jan. 1982; vol. 128(1); pp. 337-342.
Pusztai et al., Plant Lectins, 1991, Cambridge University Press, Cambridge, UK, summary only.
Sanford GL et al.; "Stimulation of vascular cell proliferation by beta-galactoside specific lectins." FASEB J. Aug. 1990; 4(11):2912-8).
Sharma et al., "Quantification of Epithelial Cell Differentiation in Mammary Glands and Carcinomas from DMBA- and MNU-Exposed Rats;" PLoS One. 2011; 6(10):e26145.
Smits BM et al., "The Gene Desert Mammary Carcinoma Susceptibility Locus Mcs1a Regulates Nr2f1 Modifying Mammary Epithelial Cell Differentiation and Proliferation" PLoS Genet. Jun. 2013; vol. 9; Issue 6 :e1003549.
Vehmeyer K et al., "Lectin induced increase in clonogenic growth of haematopoietic progenitor cells" European Journal of Haematology. Jan. 1, 1998; vol. 60(1):pp. 16-20.

(Continued)

*Primary Examiner* — Bridget E Bunner
(74) *Attorney, Agent, or Firm* — D'Ambrosio & Menon, PLLC; Usha Menon

(57) ABSTRACT

A method of treatment of disease condition resulting from deficiency of hematopoietic stem and progenitor cells and/or epidermal stem cells in skin comprising: administering to the subject suffering from said disease conditions, an effective amount of Jack bean lectin or a pharmaceutically acceptable salt thereof for increasing the abundance of hematopoietic stem cells and progenitor cells in bone marrow and/or epidermal stem cells in skin in vivo. Method of treating said conditions in a subject involves administering a single injection of lectin in a dose range of 0.5-2.0 mg/kg body weight to mouse leading to 2.815 to 3.55 fold increase in the abundance of epidermal stem cells in skin and a dose range of 8.0-10.0 mg/Kg body weight to a mouse leading to 2.36 to 6.67-fold increase in the abundance of hematopoietic stem and progenitor cells in bone marrow.

6 Claims, 3 Drawing Sheets
Specification includes a Sequence Listing.

(56) References Cited

OTHER PUBLICATIONS

Wagner JE Jr et al., "Phase I/II Trial of StemRegenin-1 Expanded Umbilical Cord Blood Hematopoietic Stem Cells Supports Testing as a Stand-Alone Graft" Cell Stem Cell; Jan. 7, 2016;18(1): pp. 144-155.

Wang YC et al., "Specific lectin biomarkers for isolation of human pluripotent stem cells identified through array-based glycomic analysis" Cell Res. Nov. 2011 Nov.; 21(11):1551-63.

Zhang Y et al., "Small molecules, big roles—the chemical manipulation of stem cell fate and somatic cell reprogramming"Journal of Cell Science; 2012 125: 5609-5620.

Fares I et al., "Cord blood expansion. Pyrimidoindole derivatives are agonists of human hematopoietic stem cell self-renewal;" Science. Sep. 2014; 19; 345(6203):1509-12.

* cited by examiner ature (Lond.), 248, 698-701; and Palacios R, J Immunol. 1982
USE OF JACK BEAN LECTIN FOR INCREASING THE ABUNDANCE OF HEMATOPOIETIC STEM CELLS AND PROGENITOR CELLS IN BONE MARROW AND/OR EPIDERMAL STEM CELLS IN SKIN IN VIVO

FIELD OF INVENTION

The invention relates to a method for increasing the abundance of hematopoietic stem cells and progenitor cells in the bone marrow and skin stem cells. More specifically the present invention provides the use of Jack bean lectin or a pharmaceutically acceptable salt thereof for increasing the abundance of hematopoietic stem cells in bone marrow and/or epidermal stem cells in skin. Advantageously the said method finds application for treating conditions including depletion of stem cells, immune suppression, leukemia, aplasia and lymphopenia. Jack bean lectin will also be useful for wound healing in burn patients and treatment of skin disorders like lupus, psoriasis, decubitus ulcers and hypohydrosis by increasing the abundance of intrinsic skin stem cells.

INCORPORATION BY REFERENCE

This application includes a sequence listing in computer readable form (a "txt" file) that is submitted herewith. This sequence listing is incorporated by reference herein.

BACKGROUND

The use of stem cells in regenerative medicine for the treatment of various human diseases is well established. The aim of regenerative medicine is to restore normal tissue functions by replenishing injured tissues with healthy cells using either cell-based therapy or by inducing endogenous repair and regeneration using small molecules. The approach of inducing endogenous repair and regeneration requires in vivo modulation of tissue-specific stem cells by therapeutic agents and enhance their abundance through activation, proliferation, differentiation, or reprogramming. Several candidate molecules like 2 deoxy-D-glucose, quercetin, baicalein, chlorophyllin, fructose 2,6-bisphosphate, rapamycin and 5-aminoimidazole-4-carboxamide ribonucleotide have been shown to enhance reprogramming and pluripotent stem cell induction (Liu K et al., Cell Chem Biol. 2016 Aug. 18; 23(8):893-916). Small molecule activators of lineage specific differentiation and lineage conversion are available for neural, cardiac, myogenic, pancreatic or hepatic tissues (Wagner J E Jr et al., Cell Stem Cell. 2016 Jan. 7; 18(1):144-55). These candidate molecules have been shown to allow ex vivo expansion of stem cells. A synthetic purine derivative, StemRegenin 1 promotes in vitro expansion of CD34+ hematopoietic stem cells in combination with cytokines involved in hematopoiesis by antagonizing aryl hydrocarbon receptor signaling (Boitano A E et al., Science. 2010 Sep. 10; 329(5997):1345-8). UM171, a pyrimidoindole derivative can expand HSC independent of AhR signaling in vitro (Fares I et al., Science. 2014 Sep. 19; 345(6203):1509-12). CD4+ T helper cells have been shown to modulate hematopoiesis by improving the HSC transplantation and increasing granulopoiesis through secreted cytokines including oncostatinM (OSM) (Broxmeyer H E et al., Immunity. 2002 June; 16(6):815-25). On the contrary, Treg cells inhibit differentiation and preserve HSC pool in the bone marrow (Bonomo et al., 2016 Frontiers in Immunology, 7: 184).

Experimental as well as translational approaches are available for modulation of intrinsic stem cell numbers, differentiation, lineage conversion, pluripotency induction and directed differentiation. These approaches include overexpression of specific transcription factors (Oct4, Nanog, Sox2, Klf4 and c-Myc, OSKM), epigenetic modifications (using 5-Azacytidine and RG108), blocking TGF-β receptor signaling, inhibition of GSK3, activation of Wnt and activation of MAPK/ERK pathway using thiazovivin (Zhang Y et al., J Cell Sci 2012 125: 5609-5620). The galactoside-specific plant lectin, Viscum album agglutinin (VAA-I) has been shown to increase the clonogenic proliferation of hematopoietic stem cells in combination with growth factors and cytokines. However, VAA-1 alone did not increase HSC proliferation (Vehmeyer K et al., Eur J Haematol. 1998 January; 60(1):16-20). Currently Granulocyte colony stimulation factor (GCSF) is used for increasing the number of hematopoietic stem cells in circulation before harvesting CD34+ cells for adoptive transfer (Brissot E et al., Bone Marrow Transplant. 2009 November; 44(9):613-5.). However, formulations are not available for increasing the abundance of intrinsic hematopoietic stem cells in the bone marrow.

In spite of various methods known in the art to dedifferentiate, transdifferentiate or re-differentiate the cells, there are very limited options for increasing the abundance of hematopoietic stem cells in the bone marrow. Formulations are not available for increasing the abundance of epidermal stem cells in the skin.

Lectins are carbohydrate-binding proteins, and their interaction with any cell is dependent on the particular types of carbohydrate moieties present on the cell surface. Blasco E et al., demonstrates that Jacalin lectin bind to β-galactoside on the surface of T-lymphocytes and it leads to proliferation of T-lymphocytes (Blasco E et al., Eur J Immunol. 1995 July; 25(7):2010-8). Sanford et al states that the lectins from peanut and mushroom, binds to β-galactoside present in the vascular cell and lead to their proliferation (Sanford G L., FASEB J. 1990 August; 4(11):2912-8). These arts further teach that the interactions between lectin and cell is both cell type specific and lectin specific. Our data shows that Jack bean lectin can bind to similar percentage of T cells, B cells and macrophages. However, it is known to induce proliferation only in T cells and not in B cells and macrophages. This data teaches that mere binding of lectin to a specific cell type is not sufficient to induce proliferation in the mammalian cells. Many lectins are known to bind to different types of tissue stem cells but they did not induce any proliferation. Eg: Peanut lectin binds mammary epithelial stem cells in rats (Sharma et al., PLoS One. 2011; 6(10):e26145; Smits B M et al., PLoS Genet. 2013 June; 9(6):e1003549; Wang Y C et al., Cell Res. 2011 November; 21(11):1551-63).

Lectins are known to bind to glycoproteins on the surface of a variety of cells including bacteria, mammalian lymphocytes and intestinal brush border cells (Pusztai et al., Plant Lectins, 1991, Cambridge University Press, Cambridge, UK.). Lectins like phytohemagglutinin from Kidney bean can cause agglutination of erythrocytes and T lymphocytes. Lectins from Jack bean and red kidney bean are known to induce proliferation in T cells (Greaves M F et al., Nature (Lond.), 248, 698-701; and Palacios R, J Immunol. 1982 January; 128(1):337-42). Peanut lectin is known to bind to mammary epithelial cells including stem cells (Kim M et al., Glycobiology. 1993 October; 3(5):447-53; Sharma et al., PLoS One. 2011; 6(10):e26145). A lectin from Kidney beans has also been shown to induce mucosal cell proliferation in the reduction and/or treatment of mucositis and/or gut lesions (CA2258503C). However, the effect of lectin from Kidney bean on stem cells has not been mentioned or claimed (CA2258503C).

The Lectin isolated from jack-bean *Canavalia ensiformis* specifically binds to various sugars, glycoproteins and glycolipids, mainly internal and non-reducing terminal α-D-mannosyl and α-D-glucosyl groups. It is widely used to characterize glycoproteins and other sugar containing entities on the surface of various cells.

The said lectin is a homotetramer made from four subunits each consisting of 235 amino acids (26.5 KDa). It is highly glycosylated and binds a divalent metal ion ($Mn^{2+}$ or $Ca^{2+}$). It can bind to glycoproteins on the surface of lymphocytes and initiate mitogenesis principally acting on T-lymphocytes by stimulating energy metabolism. The lectin interacts with different mannose containing receptors like rhodopsin, blood group markers, insulin receptor, immunoglobulins, carcinoembryonic antigen (CEA), lipoproteins and T cell receptor. It can agglutinate erythrocytes in a dose and energy dependent manner.

The said lectin induces T cell receptor cross linking, membrane reorganization and NF-kB mediated signaling leading to activation, cytokine production and cell cycle progression in T cells. It can bind to many microbes including *E. coli, B. subtilis* and also protists like *D. discoideum*.

It has been demonstrated to exhibit therapeutic effect against experimental hepatoma. It was found to sequester more hepatic tumor cells in preference to normal hepatocytes. It is identified as reproductive hazard 3, known to cause allergy, asthma or breathing difficulties, if inhaled. It may also cause toxicity to unborn child in pregnant females. It can cause skin irritation, eye irritation or irritation in the mucous membranes and upper respiratory tract. The LD50 intraperitoneal dose (rat) is 41.5 mg/kg, intravenous LD50 (mouse) is 50 mg/kg, intravenous lowest published toxic dose (TDLO) in female rats 8 days after conception is 10 mg/kg and in female mice 7 days after conception is 5 mg/kg in the literature. Lectin induces unscheduled DNA synthesis in lymphocytes.

Toxic effects of the lectin have been studied earlier in detail. At higher doses, it can cause damage to liver primarily due to activation and infiltration of T cells, production of TNF-α and IL-6 leading to sinusoidal occlusion and increased transaminase release. P selectin has been shown to play a causal role in mediating lectin mediated hepatitis. However, there is no disclosure on the effect of said lectin on increasing the abundance of hematopoietic cells of bone marrow and epidermal stem cells of skin.

There is still a need for developing effective methods of increasing the abundance of hematopoietic and skin stem cells using specific lectins from Jack bean for treating various health conditions due to depletion of said stem cells.

SUMMARY OF THE INVENTION

It is thus the primary object of the present invention to provide use of Jack bean lectin or a pharmaceutically acceptable salt thereof for increasing the abundance of hematopoietic stem cells in bone marrow and/or epidermal stem cells in skin in vivo.

Another object of the present invention is to provide a method of treatment of disease condition resulting from deficiency of hematopoietic stem and progenitor cells and/or epidermal stem cells in skin.

A further object of the present invention is to provide the method of treatment for bone marrow aplasia and deficiency of skin stem cells.

Yet another object of the present invention is to provide the method of treatment of said disease conditions comprising administering a single injection of lectin dose to increase the abundance of skin stem cells.

A further object of the present invention is to provide for manufacture of injectable formulation comprising of the Jack bean lectin or a pharmaceutically acceptable salt thereof.

Thus, according to the basic aspect of the present invention there is provided use of Jack bean lectin or a pharmaceutically acceptable salt thereof for increasing the abundance of hematopoietic stem cells in bone marrow and/or epidermal stem cells in skin.

Another aspect of the present invention provides a method of treatment of disease condition resulting from deficiency of hematopoietic stem and progenitor cells and/or epidermal stem cells in skin comprising administering to the subject suffering from the said disease condition, an effective amount of Jack bean lectin or a pharmaceutically acceptable salt thereof which is capable of increasing the abundance of hematopoietic stem cells and/or skin stem cells.

In another aspect, the present invention provides a method of treatment of said disease conditions comprising administering a therapeutically effective amount of Jack bean lectin or a pharmaceutically acceptable salt thereof in injectable formulation.

A further aspect of the present invention relates to a method of treatment of disease condition comprising administering an injectable formulation containing 1 to 250 mg of the lectin or pharmaceutical acceptable salts of the constituent peptide sequence thereof.

Yet another aspect of present invention relates to a method of treatment of said disease conditions comprising administering a single injection of lectin dose range 0.5-2.0 mg/kg body weight to mouse (which corresponds to single injection of lectin dose range 3.0 mg to 12 mg to a human weighing 72 kg) to increase the abundance of skin stem cells from 2.815±0.100% (mean±SEM) in control untreated mice to 8.097±0.938% and 9.993±0.542% in mice treated with lectin dose of 0.5 mg/kg body weight and 2 mg/kg body weight respectively.

Another aspect of the present invention relates to a method of treatment of said disease conditions comprising administering a single injection of lectin (dose range 8.0-10 mg/kg body weight) to mouse which corresponds to dose range 48.0 mg to 60.0 mg) to a human weighing 72 kg for increasing the abundance of hematopoietic stem cells in the bone marrow from 0.293±0.043% (mean±SEM) in control untreated mice to 1.956±0.592% and 0.692±0.193% in mice treated with lectin dose of 8.0 mg/kg body weight and 10 mg/kg body weight respectively.

In another aspect, the present invention relates to use of said Jack bean lectin or a pharmaceutically acceptable salt thereof for manufacture of medicament/formulation for increasing the abundance of hematopoietic stem cells in bone marrow and/or epidermal stem cells in skin.

In a further aspect the present invention relates to use of said Jack bean lectin or a pharmaceutically acceptable salt thereof for manufacture of injectable formulation.

Another aspect of the present invention relates to a method of treatment of disease conditions for treatment for bone marrow aplasia and deficiency of skin stem cells.

In a still further aspect, use of Jack bean lectin or a pharmaceutically acceptable salt thereof for manufacture of injectable formulations in form suitable to administer (i) a single injection of lectin dose range (0.5-2.0 mg/kg body weight) to mouse (which corresponds to single injection of lectin dose range 3.0 mg to 12 mg to a human weighing 72 kg) to increase the abundance of skin stem cells from 2.815±0.100% (mean±SEM) in control untreated mice to 8.097±0.938% and 9.993±0.542% in mice treated with lectin dose of 0.5 mg/kg body weight and 2 mg/kg body weight respectively and/or (ii) a single injection of lectin (dose range 8.0-10 mg/kg body weight) to mouse (which corresponds to dose range 48.0 mg to 60.0 mg to a human weighing 72 kg) for increasing the abundance of hematopoietic stem cells in the bone marrow from 0.293±0.043% (mean±SEM) in control untreated mice to 1.956±0.592% and 0.692±0.193% in mice treated with lectin dose of 8.0 mg/kg body weight and 10 mg/kg body weight respectively.

DETAILED DESCRIPTION OF THE INVENTION

Figure 1A:
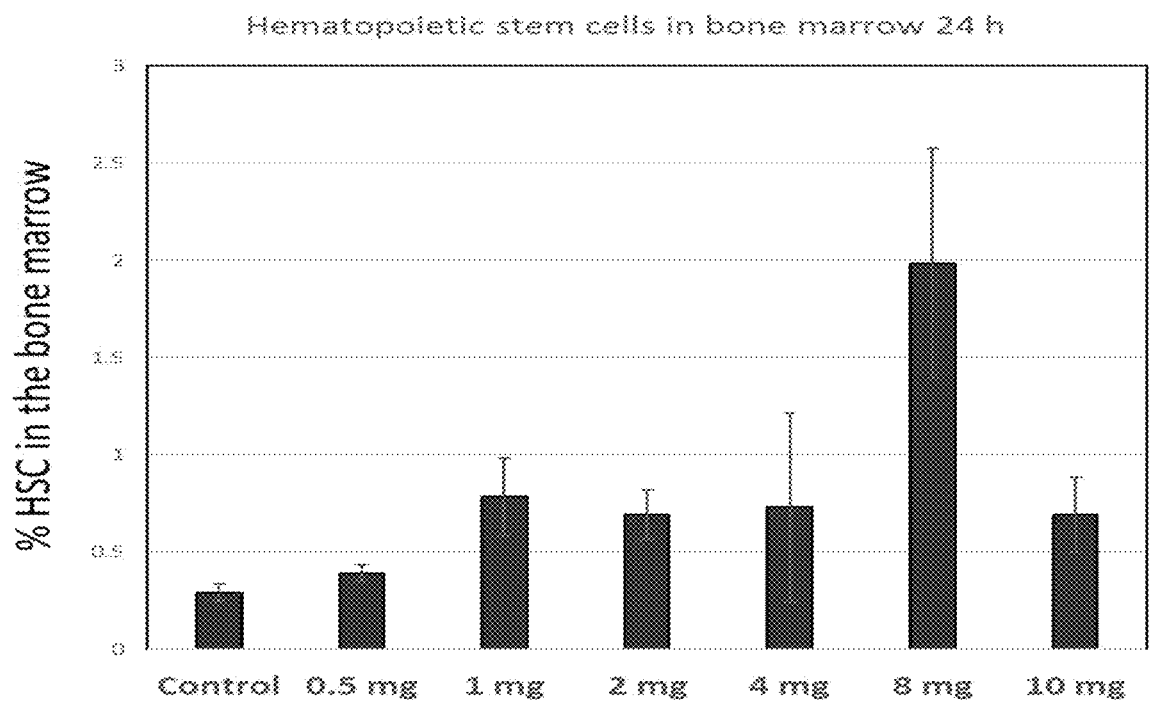
FIG. 1A represents percent hematopoietic stem cells in the bone marrow compartment of mice 24 hrs after injection of different doses of lectin.

As discussed hereinbefore, the present advancement provides for the first time the novel use of Jack bean lectin or a pharmaceutically acceptable salt thereof for increasing the abundance of hematopoietic stem cells and progenitor cells in bone marrow and/or epidermal stem cells in skin in vivo and a method of treatment involving the said lectin at a specific dose to treat conditions due to depletion of stem cells.

The said lectin derived from Jack bean or a pharmaceutically acceptable salt thereof and its constituent peptide sequence includes alkali salts or active peptide sequences from the sequence Seq. ID. NO. 1 given below.

```
Ala Asp Thr Ile Val Ala Val Glu Leu Asp Thr Tyr Pro
Asn Thr Asp Ile Gly Asp Pro Ser Tyr Pro His Ile Gly
Ile Asp Ile Lys Ser Val Arg Ser Lys LysThr Ala Lys
TrpAsn Met GlnAsnGly Lys Val Gly Thr Ala His Ile
Ile Tyr Asn Ser Val Asp Lys Arg Leu Ser Ala Val
Val Ser Tyr Pro Asn Ala Asp Ser Ala Thr Val Ser Tyr
Asp Val Asp Leu Asp Asn Val Leu Pro GluTrp Val Arg
Val Gly Leu Ser Ala Ser ThrGly Leu Tyr Lys
GluThrAsnThr Ile Leu Ser Trp Ser PheThr Ser Lys Leu
Lys Ser AsnThr His GluThrAsn Ala Leu His Phe Met
```

-continued

```
AsnGlnPhe Ser Lys Asp Gln Lys Asp Leu Ile Leu
GlnGly Asp Ala ThrThrGly Thr Asp GlyAsn Leu Glu Leu
ThrArg Val Ser SerAsn Gly Ser Pro GlnGly Ser Ser Val
GlyArg Ala Leu Phe Tyr Ala Pro Val His Ile TrpGlu
Ser Ser Ala Val Val Ala Ser PheGlu Ala Thr
PheThrPhe Leu Ile Lys Ser Pro Asp Ser His Pro Ala
Asp Gly Ile Ala PhePhe Ile Ser Asn Ile Asp Ser Ser
Ile Pro Ser Gly Ser Thr GlyArg Leu LeuGly Leu Phe
Pro Asp Ala Asn
```

As used herein, the term "hematopoietic stem cells and progenitor cells" or "HSPC's" refers to the cells in the bone marrow giving rise to all the types of blood cells, including red blood cells, B lymphocytes, T lymphocytes, natural killer cells, neutrophils, basophils, eosinophils, monocytes, and macrophages.

As used herein, the term "skin stem cells" or "SSC" refers to the cells in the skin giving rise to different layers of epidermis. These stem cells are found in the basal layer of epidermis.

As used herein, the term "increase" refers to increase in the number of cells or units, concentration, activity, intensity, frequency, population, or cellularity, whichever is applicable, by at least 10%, 20%, 30%, 40%, 50%, 60%, 70% or 80% as compared to that measured before or at the time of administration of pharmaceutical composition of the invention.

As used herein, the term "abundance of cells or units" refers to the number of cells or units in the bone marrow or skin at a given time.

The term "animal" is used herein to include all vertebrate mammals, including human.

The said lectin or a pharmaceutically acceptable salt thereof may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compositions and the pharmaceutically acceptable carriers, vehicles or diluents are then readily administered in a variety of dosage forms such as tablets, powders, lozenges, syrups, injectable solutions.

For parenteral administration, solutions of the compositions may be prepared in (for example) aqueous propylene glycol, or sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration, in this connection; the sterile aqueous media employed are all readily available and are known to those skilled in the art.

The compositions, for instance injectable, may contain e.g. 1 to 10, 10 to 100, 50 to 250 mg of the lectin or pharmaceutical acceptable salts of the constituent peptide sequence thereof.

Generally, a composition as described herein may be administered parenterally (e.g., intravenous, intramuscular, subcutaneous or intramedullary). The most preferred route of administration is intravenous.

The details of the invention are described as hereunder in the accompanying figures and illustrative examples.

Animal Maintenance:

Eight- to 9-weeks-old inbred Swiss albino mice weighing approximately 20-25 g, reared in the animal house of Bhabha Atomic Research Centre were used. Mice were housed at constant Temperature (23° C.) with a 12 h/12 h light/dark cycle and were given mouse chow and water ad libitum.

Statistical Analysis:

Data are presented as mean±SEM. Statistical analysis was done using ANOVA for comparing multiple treatment groups using GraphPad Prism 6 software.

In preparing the injectable formulation, phosphate buffered saline pH 7.2 has been used to dissolve the lyophilized lectin powder to facilitate the delivery of lectin. The solvent can be replaced by sterile isotonic saline solution.

Example 1: Assessment of Hematopoietic Stem Cell Abundance

Mice injected with lectin dose of 0.5, 1.0, 2.0, 4.0, 8.0 or 10.0 mg/kg body weight were sacrificed at indicated time points, femur bones were excised, bone marrow mononuclear cells (BM-MNC) were flushed out and counted by trypan blue viable counting method. SLAM (signaling lymphocyte activation marker) staining of BM-MNC was performed using monoclonal antibodies against lineage markers, CD48, CD244 & CD150 conjugated with different fluorochromes. Briefly, 2.5 million cells were resuspended in IMDM with 10% FBS for blocking on ice for 10 min. Cells were spin down and resuspended in antibody staining solution (20 µl per tube/0.2 µg per sample) and incubated on ice for 30 min. Cells were washed and resuspended in 1×PBS, fixed with 4% formaldehyde, washed again with PBS and Hoechst 33342 dye (10 ng/ml) was added for nuclear staining. Single stained, unstained and fluorescence minus one (FMO) control were kept for compensation during flow cytometric analysis.

FIG. 1A shows the effect of lectin at different doses on the percentage of hematopoietic stem and progenitor cells in the bone marrow of mice at 24 hrs. Maximum increase is seen at the dose of 8 mg/Kg body wt illustrated in FIG. 1B.

Figure 1B:
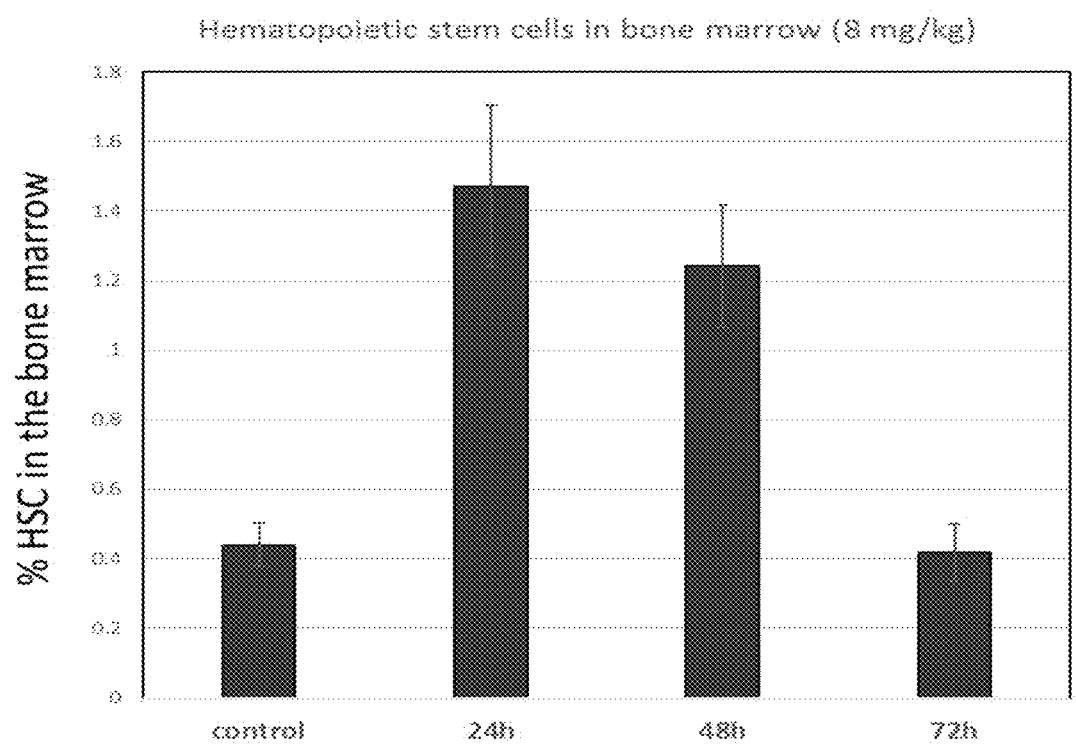
FIG. 1B represents effect of lectin on hematopoietic stem cells in the bone marrow compartment of mice injected with 8 mg/kg dose at different time points.

Injection of lectin formulation to mice significantly enhanced the abundance of Lineage$^-$ CD244$^-$CD48$^-$ CD150$^+$ hematopoietic stem cells at 24 h. This increase in the frequency of bone marrow HSCs is transient since their percentage restored back to normal levels at 72 h. (FIGS. 1A and 1B)

Example 2: Assessment of Skin Stem Cell Abundance

Mice injected with different doses of lectin were sacrificed, hair was removed, skin was excised from back side and kept for overnight incubation in 1× trypsin-EDTA solution at 4° C. Plate containing skin and trypsin solution was shifted to 37° C. and incubated for 1 h. After 1 h, complete DMEM was added to neutralize trypsin and skin cells were removed by scraping. Cells were spun down in centrifuge at 2500 rpm/5 min/RT and counted by trypan blue viable counting method. Cells were stained with fluorochrome conjugated monoclonal antibodies against CD34 and CD49f followed by fixation and Hoechst 33342 nuclear staining as described in the above protocol. Single stained and unstained controls were kept for compensation in flow cytometric data analysis.

Figure 2A:
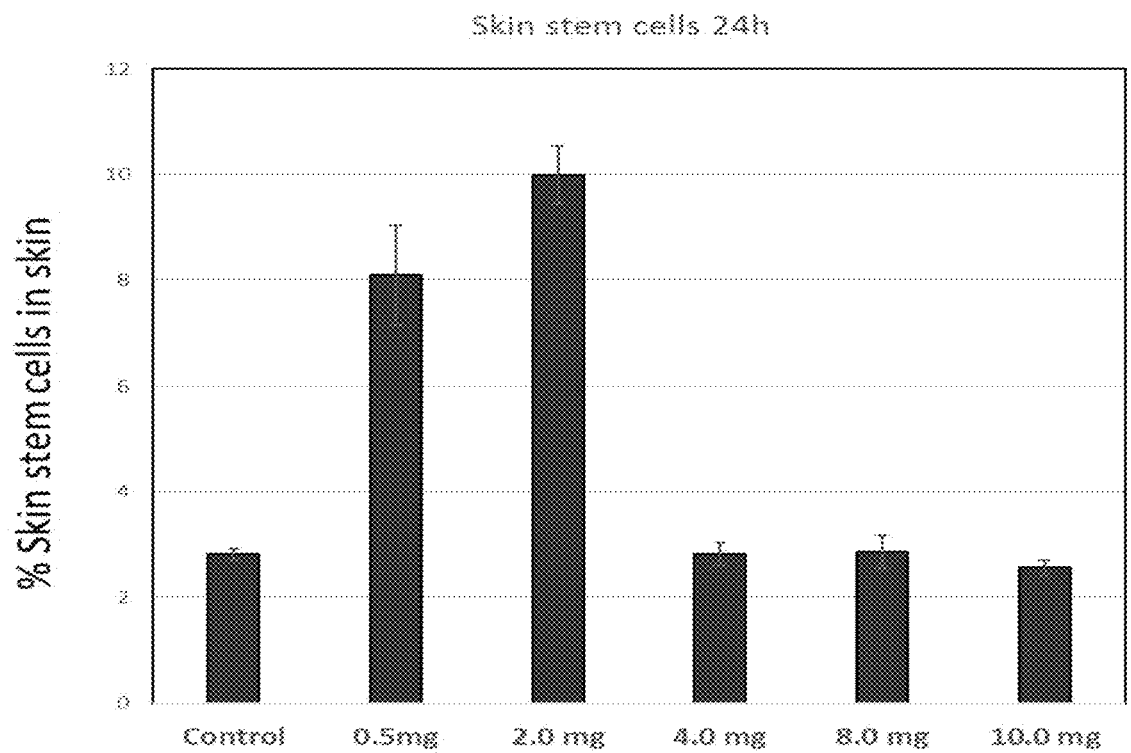
FIG. 2A illustrates effect of different doses of lectin on abundance of skin stem cells.
Figure 2B:
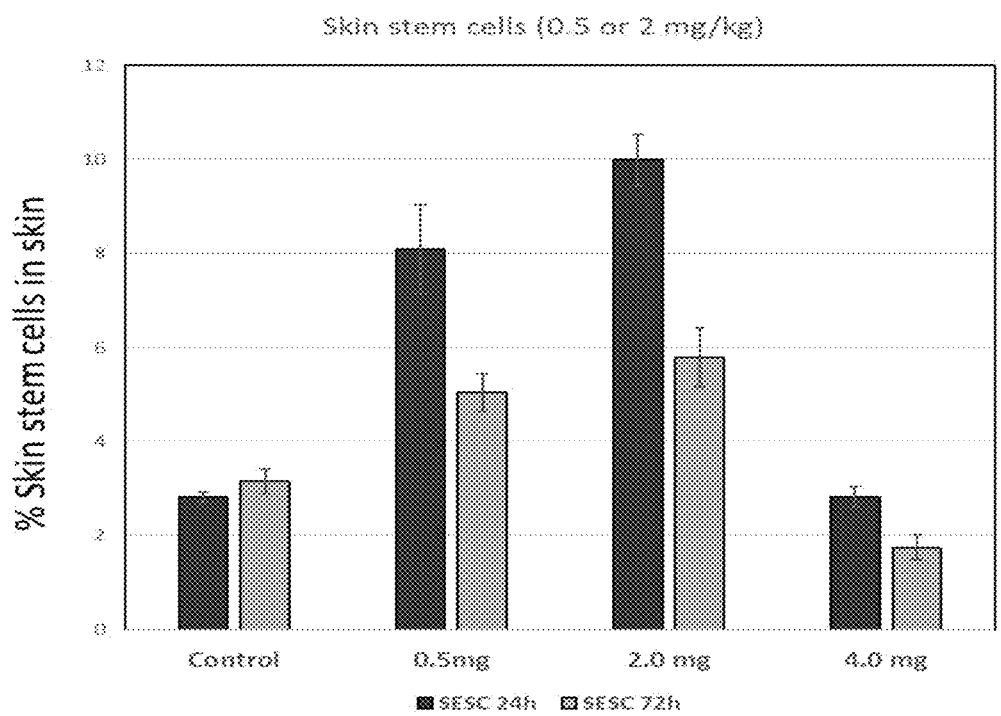
FIG. 2B illustrates changes in the abundance of skin stem cells in the skin in response to 0.5 mg/kg, 2 mg/kg or 4 mg/kg body weight dose of lectin at different time points.

FIG. 2 shows the ability of the said lectin to enhance abundance of intrinsic skin stem cells. FIG. 2A illustrates effect of different doses of lectin on abundance of skin stem cells. FIG. 2B.: Changes in the abundance of skin stem cells in the skin in response to 0.5 mg/kg or 2 mg/kg body weight dose of lectin at different time points Mice administered with two different doses of lectin formulation showed increase in the percentage of CD34+ CD49f+ skin epithelial stem cells in the skin. (FIGS. 2A and 2B).

A single dose of lectin was sufficient to achieve the increase in abundance of skin stem cells and bone marrow hematopoietic stem cells. The present findings are peculiar and unexpected because the dose required to increase the abundance of hematopoietic stem cells is almost double the dose required to enhance the abundance of skin stem cells.

Example 3: Assessment of Lectin Binding to Cells

Lectin (100 ug) was conjugated with Dylight488 using the kit (ThermoFisher Cat No 53024). Splenic lymphocytes from mice were stained with lectin (1ug) and fluorochrome conjugated monoclonal antibodies against CD3 (PE-cy5) or CD19 (PE) or CD14 (PE) followed by fixation and Hoechst 33342 nuclear staining as described in the above protocol. Single stained and unstained controls were kept for compensation in flow cytometric data analysis.

Figure 3A:
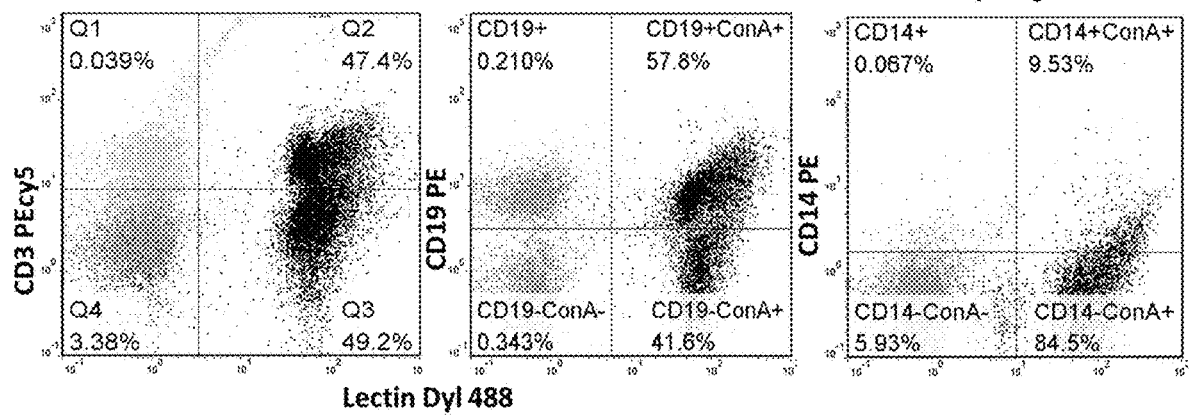
FIGS. 3A and 3B illustrate that the lectin binds to more than 96% of the CD3+ T cells, CD19+ B cells as well as CD14+ macrophages.
Figure 3B:
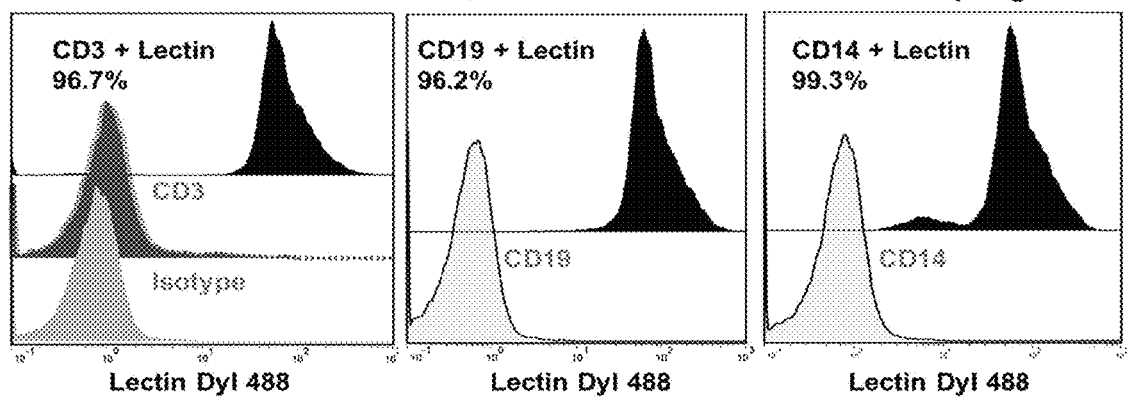

FIG. 3A shows the two parameter dot plots depicting binding of lectin to CD3+ T cells, CD19+ B cells and CD14+ macrophages. FIG. 2B illustrates overlaid flow cytometric histograms showing binding of lectin to more than 96% T cells, B cells and macrophages.

It is thus possible for the present advancement to provide for a method of treatment administering select dose of Jack bean lectin for treating disease condition resulting from deficiency of hematopoietic stem and progenitor cells in the bone marrow and/or epidermal stem cells in skin in vivo for the first time.

While several embodiments of the present invention have been described and illustrated herein, those of ordinary skill in the art will readily envision a variety of other methods for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other steps); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

We claim:

1. A method of treatment of disease condition resulting from deficiency of hematopoietic stem and progenitor cells and/or epidermal stem cells in skin comprising: administering to the subject suffering from said disease condition, an effective amount of Jack bean lectin or a pharmaceutically acceptable salt thereof which is capable of increasing the abundance of hematopoietic stem and progenitor cells and/or epidermal stem cells in skin.

2. A method of treatment of disease condition as claimed in claim 1 comprising: administering a therapeutically effective amount of Jack bean lectin or a pharmaceutically acceptable salt thereof in an injectable formulation.

3. A method of treatment of disease condition as claimed in claim 2 comprising: administering an injectable formulation containing 1 to 20 mg of the lectin or pharmaceutical acceptable salt thereof.

4. A method of treatment of disease condition as claimed in claim 2 comprising: administering a single injection of lectin in a dose range of 0.5-2.0 mg/kg body weight to a mouse which corresponds to a single injection of lectin in a dose range of 3.0 mg to 12 mg to a human weighing 72 kg to achieve an increase in the abundance of epidermal stem cells in skin.

5. A method of treatment of disease condition as claimed in claim 2 comprising: administering a single injection of lectin in a dose range of 8.0-10 mg/kg body weight to a mouse which corresponds to a dose range of 48.0 to 60.0 mg to a human weighing 72 kg to achieve an increase in the abundance of hematopoietic stem cells and progenitors cells of bone marrow.

6. A method of treatment of disease condition as claimed in claim 2 for treatment for bone marrow aplasia and deficiency of skin stem cells.

\* \* \* \* \*

SEQUENCE LISTING

```
<160> NUMBER OF SEQ ID NOS: 1

<210> SEQ ID NO 1
<211> LENGTH: 235
<212> TYPE: PRT
<213> ORGANISM: Canavalia ensiformis.

<400> SEQUENCE: 1

Ala Asp Thr Ile Val Ala Val Glu Leu Asp Thr Tyr Pro Asn Thr Asp
1               5                   10                  15

Ile Gly Asp Pro Ser Tyr Pro His Ile Gly Ile Asp Ile Lys Ser Val
            20                  25                  30

Arg Ser Lys Lys Thr Ala Lys Trp Asn Met Gln Asn Gly Lys Val Gly
        35                  40                  45

Thr Ala His Ile Ile Tyr Asn Ser Val Asp Lys Arg Leu Ser Ala Val
    50                  55                  60

Val Ser Tyr Pro Asn Ala Asp Ser Ala Thr Val Ser Tyr Asp Val Asp
65                  70                  75                  80

Leu Asp Asn Val Leu Pro Glu Trp Val Arg Val Gly Leu Ser Ala Ser
                85                  90                  95

Thr Gly Leu Tyr Lys Glu Thr Asn Thr Ile Leu Ser Trp Ser Phe Thr
            100                 105                 110

Ser Lys Leu Lys Ser Asn Thr His Glu Thr Asn Ala Leu His Phe Met
        115                 120                 125

Asn Gln Phe Ser Lys Asp Gln Lys Asp Leu Ile Leu Gln Gly Asp Ala
    130                 135                 140
```

-continued

```
Thr Thr Gly Thr Asp Gly Asn Leu Glu Leu Thr Arg Val Ser Ser Asn
145                 150                 155                 160

Gly Ser Pro Gln Gly Ser Ser Val Gly Arg Ala Leu Phe Tyr Ala Pro
            165                 170                 175

Val His Ile Trp Glu Ser Ser Ala Val Val Ala Ser Phe Glu Ala Thr
            180                 185                 190

Phe Thr Phe Leu Ile Lys Ser Pro Asp Ser His Pro Ala Asp Gly Ile
        195                 200                 205

Ala Phe Phe Ile Ser Asn Ile Asp Ser Ser Ile Pro Ser Gly Ser Thr
        210                 215                 220

Gly Arg Leu Leu Gly Leu Phe Pro Asp Ala Asn
225                 230                 235
```